(12) United States Patent
Andrews, Jr. et al.

(10) Patent No.: US 8,074,490 B2
(45) Date of Patent: Dec. 13, 2011

(54) CLANDESTINE GRAVE DETECTOR

(75) Inventors: William H. Andrews, Jr., Oliver Springs, TN (US); Cyril V. Thompson, Knoxville, TN (US); Arpad A. Vass, Oak Ridge, TN (US); Rob R. Smith, Knoxville, TN (US)

(73) Assignee: UT-Battelle LLC, Oak Ridge, TN (US)

( * ) Notice: Subject to any disclaimer, the term of this patent is extended or adjusted under 35 U.S.C. 154(b) by 0 days.

(21) Appl. No.: 11/498,705

(22) Filed: Aug. 3, 2006

(65) Prior Publication Data
US 2008/0028827 A1  Feb. 7, 2008

(51) Int. Cl.
*G01N 7/00* (2006.01)

(52) U.S. Cl. ...................................... 73/31.05

(58) Field of Classification Search ............... 73/23.2, 73/23.34, 31.01, 32.02, 31.03, 31.05; 436/124, 436/119, 139
See application file for complete search history.

(56) References Cited

U.S. PATENT DOCUMENTS

| | | | |
|---|---|---|---|
| 2,947,166 A * | 8/1960 | Palmer et al. ................... 73/40.7 |
| 3,675,466 A | 7/1972 | Linenberg | |
| 3,771,349 A * | 11/1973 | Yatabe .......................... 73/29.05 |
| 3,903,726 A * | 9/1975 | Hirosawa et al. ............... 73/23.3 |
| 4,173,886 A * | 11/1979 | Archbold et al. ............. 73/31.02 |
| 4,319,482 A * | 3/1982 | Bunner ........................ 73/152.04 |
| 4,399,688 A | 8/1983 | Dennis | |
| 4,609,875 A * | 9/1986 | Jeffers ........................... 324/455 |
| 4,617,821 A * | 10/1986 | Yokoyama et al. ............. 73/23.3 |
| 4,736,618 A * | 4/1988 | Usami et al. .................. 73/31.05 |
| 4,785,658 A * | 11/1988 | Jackson ........................ 73/31.01 |
| 5,014,541 A | 5/1991 | Sides et al. | |
| 5,277,057 A * | 1/1994 | Takashima et al. .......... 73/31.01 |
| 5,284,569 A * | 2/1994 | Lee et al. ....................... 204/425 |
| 5,296,196 A | 3/1994 | Takeshima | |
| 5,347,223 A * | 9/1994 | Krcma et al. .................. 324/455 |
| 5,363,690 A * | 11/1994 | Evangelista et al. ......... 73/31.05 |
| 5,371,467 A * | 12/1994 | Jeffers .......................... 324/464 |
| 5,435,169 A | 7/1995 | Mitra | |
| 5,448,905 A * | 9/1995 | Stetter et al. ................. 73/31.05 |
| 5,922,939 A * | 7/1999 | Cota ............................. 73/29.01 |
| 5,932,176 A * | 8/1999 | Yannopoulos et al. ......... 422/98 |

(Continued)

OTHER PUBLICATIONS

Vass et al., "Decompositional Odor Analysis Database", Journal of Forensic Sciences, vol. 49, No. 4, Jul. 2004.

(Continued)

*Primary Examiner* — John Fitzgerald
(74) *Attorney, Agent, or Firm* — Quarles & Brady LLP

(57) ABSTRACT

An apparatus and a method for detecting a burial site of human remains are disclosed. An air stream is drawn through an air intake conduit from locations near potential burial sites of human remains. The air stream is monitored by one or more chemical sensors to determine whether the air stream includes one or more indicator compounds selected from halogenated compounds, hydrocarbons, nitrogen-containing compounds, sulfur-containing compounds, acid/ester compounds, oxygen-containing compounds, and naphthalene-containing compounds. When it is determined that an indicator compound is present in the air stream, this indicates that a burial site of human remains is below or nearby. Each sensor may be in electrical communication with an indicator that signals when the sensor has detected the presence of the indicator compound in the air stream. In one form, the indicator compound is a halogenated compound and/or a hydrocarbon, and the presence of the halogenated compound and/or the hydrocarbon in the air stream indicates that a burial site of human remains is below or nearby.

28 Claims, 2 Drawing Sheets

U.S. PATENT DOCUMENTS

| | | | |
|---|---|---|---|
| 6,341,629 B1* | 1/2002 | Clark et al. | 141/83 |
| 6,824,394 B1* | 11/2004 | Brundage | 439/65 |
| 6,844,197 B1* | 1/2005 | Doleman et al. | 436/151 |
| 6,952,945 B2* | 10/2005 | O'Brien | 73/23.35 |
| 7,003,405 B1* | 2/2006 | Ho | 702/32 |
| 7,041,256 B2* | 5/2006 | Wang et al. | 422/94 |
| 7,159,445 B2* | 1/2007 | Bohm et al. | 73/23.2 |
| 7,168,423 B2* | 1/2007 | Nonaka | 123/703 |
| 7,533,558 B2* | 5/2009 | Flaherty et al. | 73/23.3 |
| 7,571,634 B2* | 8/2009 | Grosse Bley | 73/23.21 |
| 7,588,726 B1* | 9/2009 | Mouradian et al. | 422/83 |
| 2002/0026822 A1* | 3/2002 | Reading et al. | 73/31.05 |
| 2003/0015019 A1* | 1/2003 | O'Brien | 73/23.2 |
| 2004/0053290 A1* | 3/2004 | Terbrueggen et al. | 435/6 |
| 2004/0069046 A1* | 4/2004 | Sunshine et al. | 73/23.34 |
| 2005/0126264 A1* | 6/2005 | Komninos | 73/40.5 A |
| 2005/0191757 A1* | 9/2005 | Melker et al. | 436/164 |
| 2007/0113686 A1* | 5/2007 | Desrochers et al. | 73/863.33 |

OTHER PUBLICATIONS

The Informant, Refrigerant Leak Detector, Instruction 19-9210, Operation and Maintenance, Bacharach Inc., Rev. 4—Apr. 2001.

Leakator 10, Instruction 19-9167, Combustible Gas Detector, Bacharach Inc., Rev. 10—May 2002.

Thompson, Cyril V. and Marcus B. Wise, "Effects of Silcosteel® Transfer Line on the Sampling of Volatile Organic Compounds", Field Analytical Chemistry and Technology 2(5):309-314, 1998.

* cited by examiner

CLANDESTINE GRAVE DETECTOR

STATEMENT REGARDING FEDERALLY SPONSORED RESEARCH

This invention was made with United States Government support under Contract No. DE-AC05-00OR22725 between the United States Department of Energy and U.T. Battelle, LLC. The United States Government has certain rights in this invention.

CROSS-REFERENCES TO RELATED APPLICATIONS

Not Applicable.

BACKGROUND OF THE INVENTION

1. Field of the Invention

This invention relates to a man-portable, chemical sensor capable of detecting clandestine burial sites of human remains and to a method for detecting clandestine burial sites of human remains.

2. Description of the Related Art

Locating clandestine graves, identification of victims (development of biological profiles from unidentified persons) and odor recognition (in locating and identifying individuals) are still very difficult, costly and time consuming tasks which impact law enforcement, intelligence and military operations around the world. The detection of buried human remains (which may have been buried in a clandestine act where human remains are buried in a hastily dug, shallow grave) is most often accomplished with the aid of manual probing techniques, ground-penetrating radar, or canines trained to detect human remains.

Manual probing is very inexpensive and is used to locate disturbed soil regions, but cannot confirm the presence of a corpse and can only be used in small areas. Ground-penetrating radar is usually expensive and also locates areas of disturbed soil. Under ideal conditions, and if the grave is very fresh, ground-penetrating radar can sometimes indicate the presence of a corpse, but radar can be easily fooled by objects in the environment (e.g., roots, stumps, rocks, debris, man-made objects, etc.) and requires a significant amount of training to interpret the signals indicative of clandestine graves. Canines that detect human remains, commonly referred to as cadaver dogs, have been minimally represented in the law enforcement canine population across the United States. For a variety of reasons, this canine detector specialty has not been given the attention that is afforded both the explosive and narcotic specialties. The current concern facing cadaver dog units is that training is inadequate since it is unknown to what odor signals the dogs respond to when alerting and the alerting may not completely be in response to odor. This jeopardizes search and seizure as well as probable cause rules currently established for search warrants and chain of custody. Many agencies usually employ a combination of these methods when searching for clandestine graves, mass graves or missing persons which also results in an increased cost, significant utilization of man-hours, logistic and time concerns.

In an article entitled "Decompositional Odor Analysis Database" in the *Journal of Forensic Sciences*, Vol. 49, No. 4, July 2004, Vass et al. reported a study in which the volatile and semivolatile compounds that migrate upward from human burials to the soil surface during decomposition were identified. The study sought to determine the chemical markers associated with odor of human decomposition, primarily aimed at legitimizing the training efforts of cadaver locating dogs. This study focused on human remains in graves of various depths and of various ages (fresh—15 years old) under a variety of environmental conditions. The results of this study has been a collection of different chemical compounds liberated from human decomposition in burial situations, of which only a fraction make it to the surface in a reproducible fashion regardless of the depth of burial and age of the grave.

However, there is still a need for a man-portable clandestine grave detector that will take the guess-work out of current methods using canines and ground-penetrating radar, which have historically been unreliable.

SUMMARY OF THE INVENTION

The need for an improved method and apparatus for detecting clandestine burial sites of human remains is met by the present invention.

In one aspect, the invention provides an apparatus for detecting burial sites of human remains. The apparatus includes an air intake conduit, means for drawing an air stream through the air intake conduit from a location near or above a potential burial site of human remains, a halogen sensor positioned to contact the air stream in the air intake conduit, and a hydrocarbon sensor positioned to contact the air stream in the air intake conduit. The halogen sensor detects the presence of a halogenated compound in the air stream, and the hydrocarbon sensor detects the presence of a hydrocarbon in the air stream. The presence of halogenated compounds and hydrocarbons near or above a burial site indicates that human remains may be buried below or nearby.

The apparatus may include a concentrator for increasing the concentration of one or more halogenated compounds and/or one or more hydrocarbons in the air stream to increase the sensitivity of the apparatus. The concentrator may be located upstream of the halogen sensor and the hydrocarbon sensor. In one form, the concentrator includes a sorbent for adsorbing one or more halogenated compounds and/or one or more hydrocarbons in the air stream and means for desorbing the adsorbed compounds from the sorbent. The means for desorbing may be a heater located adjacent the sorbent for thermally desorbing the adsorbed compound(s) from the sorbent by raising the temperature of the sorbent. A switch for activating and deactivating the heater may be provided for allowing time for adsorption of the compounds of interest on the sorbent before the thermal desorption process is initiated.

The apparatus may include a halogen visual indicator in electrical communication with the halogen sensor, and/or a hydrocarbon visual indicator in electrical communication with the hydrocarbon sensor, and/or a halogen audible indicator in electrical communication with the halogen sensor, and/or a hydrocarbon audible indicator in electrical communication with the hydrocarbon sensor. The halogen visual indicator lights up when the halogen sensor has detected the presence of a halogenated compound in the air stream. The hydrocarbon visual indicator lights up when the hydrocarbon sensor has detected the presence of a hydrocarbon in the air stream. The halogen audible indicator emits an audible signal when the halogen sensor has detected the presence of a halogenated compound in the air stream. The hydrocarbon audible indicator emits an audible signal when the hydrocarbon sensor has detected the presence of a hydrocarbon in the air stream.

In the apparatus, the means for drawing an air stream through the air intake conduit may be a fan or a pump. The apparatus may further include an additional sensor positioned to contact the air stream in the air intake conduit. The additional sensor is provided for detecting the presence in the air stream of a compound selected from the group consisting of nitrogen-containing compounds, sulfur-containing compounds, acid/ester compounds, oxygen-containing compounds, and naphthalene-containing compounds. The presence of any of these compounds near or above a burial site indicates that human remains may be buried below.

The apparatus may further include a receiver on the apparatus for receiving position data from a global positioning system satellite when the apparatus is directed near potential burial sites. A processor is in communication with the halogen sensor for receiving halogen levels, in communication with the hydrocarbon sensor for receiving hydrocarbon levels, and in communication with the receiver for receiving position data. The processor outputs signals indicative of halogen levels and hydrocarbon levels at positions near the potential burial sites. In this manner, a team of searchers, each with his own apparatus can perform a grid search and produce a map of airborne halogen and hydrocarbon compound concentrations.

In another aspect, the invention provides a method for detecting a burial site of human remains. In the method, an air stream is drawn through an air intake conduit from locations near or above potential burial sites of human remains. The air stream is monitored to determine whether in the air stream there is present an indicator compound selected from the group consisting of halogenated compounds, hydrocarbons, nitrogen-containing compounds, sulfur-containing compounds, acid/ester compounds, oxygen-containing compounds, and naphthalene-containing compounds. When it is determined that the indicator compound is present in the air stream, this indicates a burial site of human remains may be below or nearby. The step of monitoring the air stream may include providing a sensor in the air intake conduit. The sensor is in electrical communication with an indicator that signals when the sensor has detected the presence of the indicator compound in the air stream. The indicator may be a visual indicator that lights up when the sensor has detected the presence of the indicator compound in the air stream, and/or the indicator may be an audible indicator that emits an audible signal when the sensor has detected the presence of the indicator compound in the air stream.

In one version of the method, the indicator compound is a halogenated compound, and the step of monitoring the air stream includes providing a halogen sensor in the air intake conduit wherein the halogen sensor is in electrical communication with an indicator that signals when the halogen sensor has detected the presence of the halogenated compound in the air stream. In another version of the method, the indicator compound is a hydrocarbon, and the step of monitoring the air stream includes providing a hydrocarbon sensor in the air intake conduit wherein the hydrocarbon sensor is in electrical communication with an indicator that signals when the hydrocarbon sensor has detected the presence of the hydrocarbon in the air stream. The method may include the step of recording a concentration level of indicator compounds (e.g., halogenated compounds or hydrocarbons) at a number of locations near potential burial sites.

In yet another version of the method, the indicator compound is concentrated in the air stream before the air stream contacts the sensor to increase the sensitivity of the method. The indicator compound may concentrated in the air stream by adsorbing the indicator compound on a sorbent and thereafter desorbing the indicator compound from the sorbent. Thermal desorption may be used for desorbing the indicator compound from the sorbent.

In yet another aspect, the invention provides a method for detecting a burial site of human remains. In the method, an air stream is drawn through an air intake conduit from locations near or above potential burial sites of human remains. The air stream is monitored to determine whether a halogenated compound is present in the air stream, and the air stream is also monitored to determine whether a hydrocarbon is present in the air stream. When it is determined that a halogenated compound or a hydrocarbon is present in the air stream, this indicates a burial site of human remains may be below or nearby. The step of monitoring the air stream to determine whether a halogenated compound is present in the air stream may include providing a halogen sensor in the air intake conduit wherein the halogen sensor is in electrical communication with an indicator that signals when the halogen sensor has detected the presence of the halogenated compound in the air stream. The step of monitoring the air stream to determine whether a hydrocarbon is present in the air stream may include providing a hydrocarbon sensor in the air intake conduit wherein the hydrocarbon sensor is in electrical communication with an indicator that signals when the hydrocarbon sensor has detected the presence of the hydrocarbon in the air stream.

Thus, it is an advantage of the present invention to provide an apparatus for detecting burial sites of human remains.

It is another advantage to provide a method for detecting a burial site of human remains.

These and other features, aspects, and advantages of the present invention will become better understood upon consideration of the following detailed description, drawings and appended claims.

DETAILED DESCRIPTION OF THE INVENTION

The invention provides an apparatus and a method for detecting a burial site of human remains. An air stream is drawn through an air intake conduit from locations near or above potential burial sites of human remains. The air stream is monitored by one or more chemical sensors to determine whether the air stream includes one or more indicator compounds selected from halogenated compounds, hydrocarbons, nitrogen-containing compounds, sulfur-containing compounds, acid/ester compounds, oxygen-containing compounds, and naphthalene-containing compounds. When it is determined that an indicator compound is present in the air stream, this indicates that a burial site of human remains may be below.

Non-limiting examples of indicator compounds that indicate that a burial site of human remains may be below include: (1) Cyclic Hydrocarbons such as 1,4 dimethyl benzene; 1,2 dimethyl benzene; Ethyl benzene; Toluene; Styrene; 1-methyl-2-ethyl benzene; and C4-benzene; (2) Non-Cyclic Hydrocarbons such as heptane; 2-methyl pentane; and undecane; (3) Nitrogen Compounds such as methenamine; and benzonitrile; (4) Sulfur Compounds such as sulfur dioxide; carbon disulfide; benzothiazole; 2,4-dimethylthiane, S,S-dioxide; dimethyl trisulfide; and dimethyl disulfide; (5) Acid/ester Compounds such as hexadecanoic acid, methyl ester;

(6) Oxygen Compounds such as decanal; benzene methanol, a,a dimethyl; 1-Hexanol, 2-ethyl; benzaldehyde; nonanal; benzene (1-methoxypropyl); and 2-propanone; (7) Halogen Compounds such as trichloromonofluoromethane; chloroform; trichloroethene; tetrachloroethene; dichlorodifluoromethane; dichlorotetrafluoroethane; trichloroethane; and carbon tetrachloride; and (8) naphthalene-containing compounds such as 1-methyl naphthalene; and naphthalene.

Figure 1:
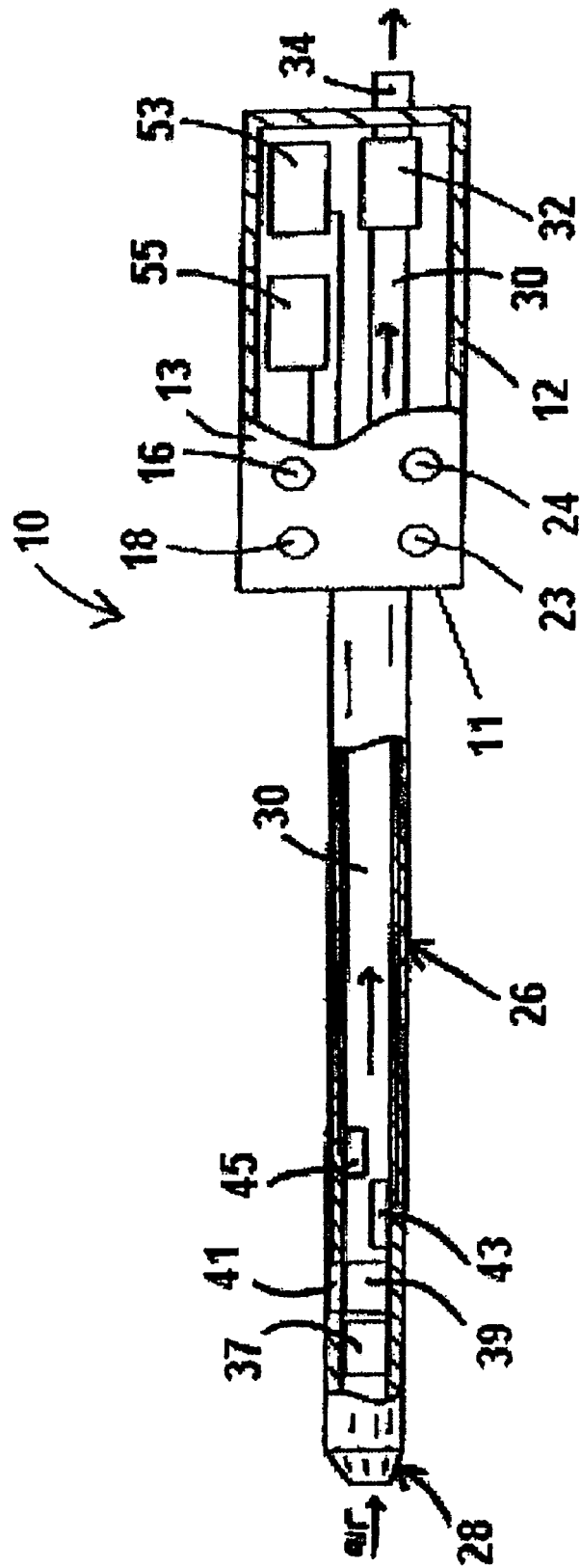
FIG. 1 is a top view, partially in cross-section, of an example apparatus according to the invention.
Figure 2:
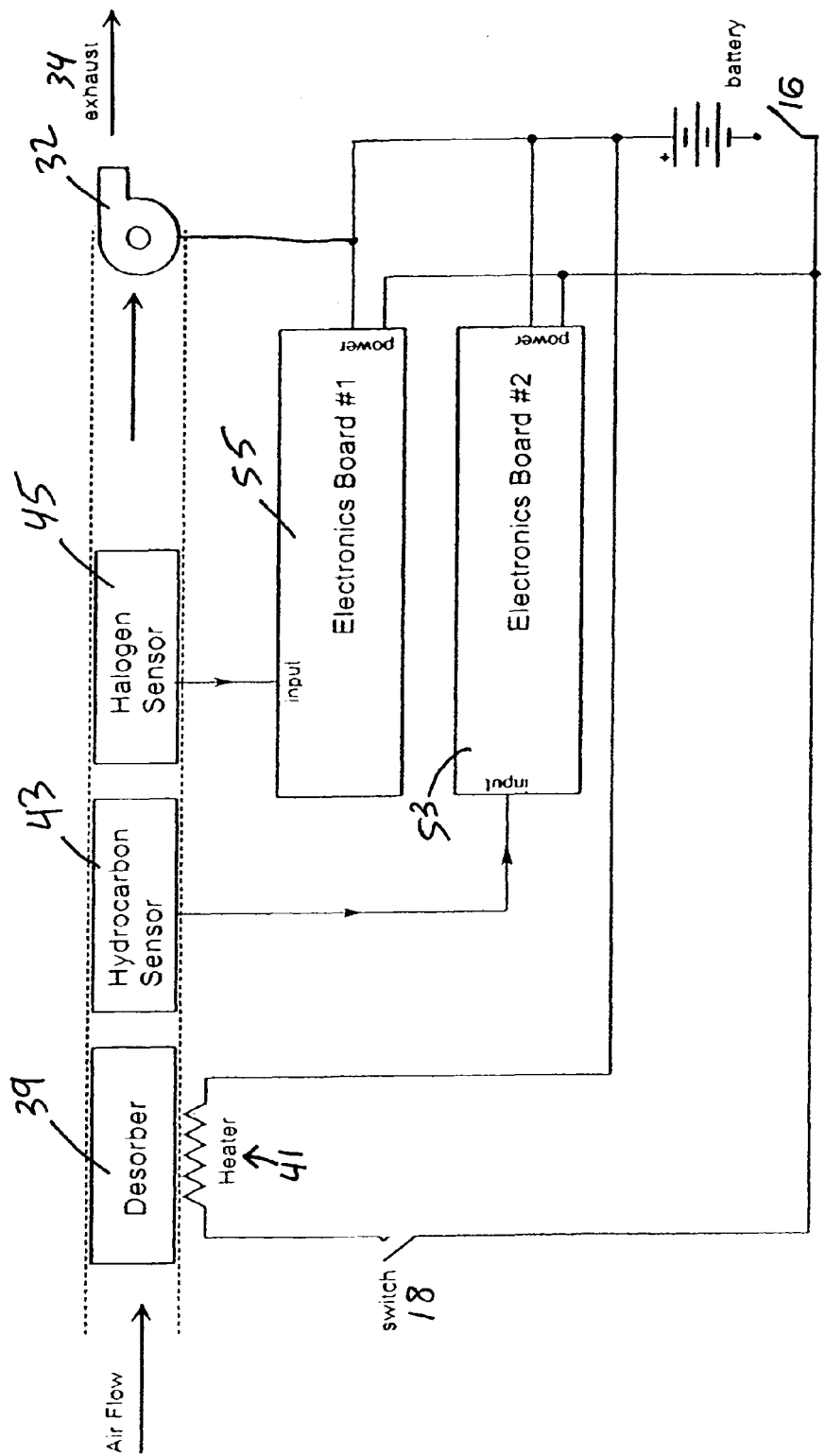
FIG. 2 is a schematic of the apparatus of FIG. 1.

Referring now to FIGS. 1 and 2, there is shown an example man-portable clandestine grave detector apparatus 10 according to the invention and a schematic of the apparatus 10, respectively. The example apparatus 10 is configured to detect halogenated compounds and hydrocarbons near or above a burial site of human remains. The apparatus 10 includes a plastic housing 11 formed from a rectangular box-shaped lower section 12 and a top section 13 that is assembled to the box-shaped lower section 12 by suitable means such as screws. The top section 13 has an on-off power button 16 for the apparatus 10, a button 18 that switches on and off a heater 41 (described below), a hydrocarbon indicator 23 that lights up upon detection of a hydrocarbon, and a halogen indicator 24 that lights up upon detection of a halogen.

The apparatus 10 also includes a flexible hollow tubular snorkel 26 with a nozzle 28. The snorkel 26 and nozzle 28 form part of an air intake conduit 30 that runs from the nozzle through the snorkel 26 to a pump 32 and out of an exhaust tube 34. The pump 32 draws an air stream through the air intake conduit 30. The air stream then exits through the exhaust tube 34. In an alternative embodiment, the pump 32 is replaced with a fan for drawing an air stream through the air intake conduit 30. In the air intake conduit 30 of the snorkel 26, there is positioned an air filter media 37, a sorbent cartridge 39, a heater 41, a hydrocarbon sensor 43 and a halogen sensor 45. The hydrocarbon sensor 43 is in electrical communication with an electronics circuit board 53 which is in electrical communication with the hydrocarbon indicator 23, and the halogen sensor 45 is in electrical communication with an electronics circuit board 55 which is in electrical communication with the halogen indicator 24. The air stream passes from the nozzle 28 through the air filter media 37 (which serves to remove particulate matter from the air stream), through the sorbent cartridge 39, over the hydrocarbon sensor 43 and over the halogen sensor 45.

The sorbent cartridge 39 and the heater 41 (which is located adjacent and/or touching the sorbent cartridge 39) work together to concentrate halogenated compounds and hydrocarbons in the air stream before the halogenated compounds and hydrocarbons contact the hydrocarbon sensor 43 and the halogen sensor 45. The sorbent cartridge 39 may be a cylindrical tube packed with a suitable sorbent that adsorbs halogenated compounds and hydrocarbons as the air stream passes through the tube of the sorbent cartridge 39. By pressing button 18, the heater 41 is switched on and heat is applied to the sorbent thereby thermal desorbing the adsorbed halogenated compounds and hydrocarbons from the sorbent in the sorbent cartridge 39. The type of heater selected may vary. For example, the heater 41 may be a plate-type resistance heater, or a microwave heater, or a hot air heater. Alternatively, the sorbent cartridge 39 may include a metallic tube that is heated by passing current directly through the metallic wall of the tube. In an alternative embodiment, the heater is activated by a programmable controller that activates the heater according to a timed schedule. Regardless of the sorbent cartridge and heater chosen, the concentration of halogenated compounds and hydrocarbons in the air stream is increased by adsorbing the halogenated compounds and hydrocarbons on the sorbent and thereafter desorbing a higher concentration of the halogenated compounds and hydrocarbons from the sorbent into the air stream. By increasing the concentration of one or more halogenated compounds and/or one or more hydrocarbons in the air stream, the sensitivity of the apparatus 10 is increased as certain hydrocarbon sensors and halogen sensors may not detect low levels of hydrocarbons and halogens, respectively.

The hydrocarbon sensor 43 may be selected from many different types of hydrocarbon sensors. One example hydrocarbon sensor is a semiconductor detector based on a sintered metal oxide. These detectors operate to indicate the presence of hydrocarbon gases as a result of their marked decrease in electrical resistance in the presence of hydrocarbons. A current is passed through the detector and the change in conductivity is measured for use in determining the presence of hydrocarbons. Example hydrocarbon sensors are available from Figaro USA Inc., Glenview, Ill., USA. See, also, U.S. Pat. No. 5,296,196 for another example hydrocarbon sensor. The change in conductivity of the sensor can be monitored continuously, and a suitable electric circuit in the electronics circuit board 53 can be used to light up the hydrocarbon indicator 23 upon detection of a hydrocarbon.

The halogen sensor 45 may be selected from many different types of halogen sensors. One example halogen sensor is a heated diode such as that described in U.S. Pat. No. 5,932, 176. This type of halogen sensor includes a collector with an oxidation-resistant noble metal wire with a nonreactive electrically insulating oxide coating wound into a helical coil to define a cylindrical space. A conductive noble metal pin is positioned within the cylindrical space. Finely divided sintered sodium titanate fills the space between the coil and the pin. A circuit with leads connected to a battery is provided for causing an electrical current to flow in the coil to raise the temperature thereof. Another circuit including leads is provided for applying a voltage between the coil and pin and sensing a change in current between the coil and pin indicative of the presence of a halogen or halogenated compound. The change in current of the sensor can be monitored continuously, and a suitable electric circuit in the electronics circuit board 55 can be used to light up the halogen indicator 24 upon detection of a halogen.

Having described the components of an example man-portable clandestine grave detector apparatus 10 according to the invention, the operation of the apparatus 10 can be described in more detail with reference to FIGS. 1 and 2. A user holds the apparatus 10 by way of the plastic housing 11 (which may include a handle that is not shown). The user presses the on-off power button 16 of the apparatus 10 to provide electricity from a battery to power up the pump 32, the hydrocarbon sensor 43, the electronics circuit board 53, the halogen sensor 45 and the electronics circuit board 55. The pump 32 draws an air stream through the nozzle 28, through the air filter media 37, through the sorbent cartridge 39, over the hydrocarbon sensor 43 and over the halogen sensor 45. The user then places the nozzle 28 at locations near or above a potential burial site of human remains drawing in an air stream from these locations.

After a period of time, the user presses button 18 and the heater 41 is switched on and heat is applied to the sorbent thereby thermal desorbing any adsorbed halogenated compounds and hydrocarbons from the sorbent in the sorbent cartridge 39. The desorbed compounds enter the air stream and pass over the hydrocarbon sensor 43 and the halogen sensor 45. The electronics circuit board 53 receives electrical signals from the hydrocarbon sensor 43 and includes a suitable electric circuit that can be used to light up the hydrocarbon indicator 23 upon detection of a hydrocarbon. Optionally, the electronics circuit board 53 includes a suitable electric circuit that can be used to cause an audible indicator to emit an audible signal upon detection of a hydrocarbon. Likewise, the electronics circuit board 55 receives electrical signals from the halogen sensor 45 and includes a suitable electric circuit that can be used to light up the halogen indicator 24 upon detection of a halogen. Optionally, the electronics circuit board 55 includes a suitable electric circuit that can be used to cause an audible indicator to emit an audible signal upon detection of a halogen. The detection of a halogen and/or hydrocarbon near or above a potential burial site of human remains indicates that a burial site of human remains may be below.

A prototype of the example man-portable clandestine grave detector apparatus 10 according to the invention was constructed as follows. A hydrocarbon sensor and a halogen sensor were used simultaneously to provide greater selectivity in chemical detection. A sorbent cartridge was added to the clandestine grave detector to permit collection and concentration of the very volatile chemicals of interest, followed by thermal desorption of the sorbent bed (Carbosieve SIII) and subsequent analysis by both the sensors. Micro-thermally desorbed sorbents were found to be beneficial. A pump was added to the device to provide the sample flows necessary through the sorbent bed. The electronics boards were mounted in a common plastic enclosure along with a pump for drawing air through the sensors.

The hydrocarbon sensor and the halogen sensor were mounted in a flexible snorkel. The hydrocarbon sensor was a semiconductor type sensor that has a sensitivity of 50 ppm methane at a minimum. The halogen sensor was a heated diode with a sensitivity of 14 g/yr of R-134a. The desorber was mounted at the fore end of the snorkel so that air is drawn through the filter media before it reaches the two sensors. The distance between the desorber and the sensors was minimized to reduce sensor response time. The indicator lights of the electronics boards were visible through a clear lid on the plastic enclosure and the two pushbutton controls (on-off and heater) were accessible through small holes in the lid. Alarm tones indicating halogens and hydrocarbons were clearly audible through speakers in the enclosure.

The prototype was tested with various concentrations of trichloroethylene, a halogenated hydrocarbon, which elicited a response from both sensors on the device at levels of 100 ppb. Field testing of the prototype at the University of Tennessee's Decay Research Facility was met with success.

It can be seen that the prototype and the example man-portable clandestine grave detector apparatus 10 only include a hydrocarbon sensor and a halogen sensor. It can be appreciated that the prototype and the described apparatus 10 have been presented for the purposes of illustration. It should be appreciated that additional sensors can be placed in the snorkel 26. For example, sensors for nitrogen-containing compounds, sulfur-containing compounds, acid/ester compounds, oxygen-containing compounds, and naphthalene-containing compounds can be placed in the snorkel and these sensors can be electrically connected to a suitable indicator (e.g., visual and/or audible) to indicate that a burial site of human remains may be below or nearby.

In another embodiment of the apparatus of the invention, the apparatus has GPS capability and a wireless link to a computer located nearby. In this manner, a team of searchers, each with his own apparatus can perform a grid search and produce a map of airborne halogen and hydrocarbon compound concentrations. The computer can archive the information, and perform further analysis based on developed models, and relay the data to other sites. In this embodiment of the apparatus, a GPS receiver is mounted on the apparatus. The receiver uses the global positioning system (GPS) to provide exact and continually updated information concerning the position of the apparatus in global coordinates. Such receivers are commercially available, and may include differential correction methods to integrate data from a number of satellites and reference stations. The receiver can receive from GPS satellites and provide the correct latitude, longitude and altitude of the apparatus, along with the precise time and date, and the speed and track over the ground of the apparatus. Such data can then be transmitted to a processor on the apparatus. The processor may be any type of processor which can receive the required data and process it. The processor also receives data on the hydrocarbon levels from the electronics circuit board 53 and data on the halogen levels from the electronics circuit board 55. As the apparatus passes over the ground, the processor transmits to the computer, by wireless link, signals including position data and hydrocarbon and halogen levels associated with each position such that the hydrocarbon and halogen levels at each position can be reviewed after the apparatus is directed over the ground.

Therefore, it can be seen that the invention provides a man-portable, chemical sensor capable of detecting clandestine burial sites of human remains and provides a method for detecting clandestine burial sites of human remains. The invention may be used by law enforcement agencies interested in finding the bodies of murder victims, etc. The invention may also be used to locate bodies in earthquake ruins and collapsed buildings. In this regard, the term "burial sites of human remains" as used herein should be interpreted to include natural disaster ruins and collapsed buildings.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. An apparatus for detecting burial sites of human remains, the apparatus comprising:
   a housing for containing sensor electronics;
   an air intake conduit including a snorkel positioned upstream of the housing;
   means for drawing an air stream through the air intake conduit from a location near a potential burial site of human remains;
   a halogen sensor positioned to contact the air stream in the air intake conduit, the halogen sensor detecting the presence of a halogenated compound in the air stream; and
   a hydrocarbon sensor positioned to contact the air stream in the air intake conduit, the hydrocarbon sensor detecting the presence of a hydrocarbon in the air stream,
   wherein the halogen sensor and the hydrocarbon sensor are positioned in the snorkel upstream of the housing at an end section of the snorkel opposite the housing, and
   wherein the halogen sensor and the hydrocarbon sensor are positioned in the snorkel spaced downstream from an end of the snorkel, and
   wherein determining that a halogenated compound or a hydrocarbon is present in the air stream indicates a burial site of human remains.

2. The apparatus of claim 1 further comprising one or more of the following:
   a halogen visual indicator in electrical communication with the halogen sensor, the halogen visual indicator lighting up when the halogen sensor has detected the presence of a halogenated compound in the air stream;

a hydrocarbon visual indicator in electrical communication with the hydrocarbon sensor, the hydrocarbon visual indicator lighting up when the hydrocarbon sensor has detected the presence of a hydrocarbon in the air stream;

a halogen audible indicator in electrical communication with the halogen sensor, the halogen audible indicator emitting an audible signal when the halogen sensor has detected the presence of a halogenated compound in the air stream; and a hydrocarbon audible indicator in electrical communication with the hydrocarbon sensor, the hydrocarbon audible indicator emitting an audible signal when the hydrocarbon sensor has detected the presence of a hydrocarbon in the air stream.

3. The apparatus of claim 1 wherein the means for drawing an air stream through the air intake conduit comprises a fan or a pump.

4. The apparatus of claim 1 further comprising:
an additional sensor positioned in the snorkel to contact the air stream in the air intake conduit, the additional sensor detecting the presence in the air stream of a compound selected from the group consisting of nitrogen-containing compounds, sulfur-containing compounds, acid/ester compounds, oxygen-containing compounds, and naphthalene-containing compounds.

5. The apparatus of claim 1 further comprising:
a receiver on the apparatus for receiving position data from a global positioning system satellite when the apparatus is directed near potential burial sites; and
a processor in communication with the halogen sensor for receiving halogen levels, in communication with the hydrocarbon sensor for receiving hydrocarbon levels, and in communication with the receiver for receiving position data, the processor outputting signals indicative of halogen levels and hydrocarbon levels at positions near the potential burial sites.

6. The apparatus of claim 1 wherein the hydrocarbon sensor is located upstream of the halogen sensor.

7. The apparatus of claim 1 further comprising:
a concentrator for increasing the concentration of at least one of any halogenated compounds in the air stream, the concentrator being located in the snorkel upstream of the halogen sensor.

8. The apparatus of claim 7 wherein the concentrator comprises:
a sorbent for adsorbing the at least one halogenated compound, and
means for desorbing the at least one halogenated compound from the sorbent.

9. The apparatus of claim 8 wherein the means for desorbing comprises:
a heater located adjacent the sorbent for desorbing the at least one halogenated compound from the sorbent by raising the temperature of the sorbent, and
a switch for activating and deactivating the heater.

10. The apparatus of claim 1 further comprising:
a concentrator for increasing the concentration of at least one of any hydrocarbon in the air stream, the concentrator being located in the snorkel upstream of the hydrocarbon sensor.

11. The apparatus of claim 10 wherein the concentrator comprises:
a sorbent for adsorbing the at least one hydrocarbon, and
means for desorbing the at least one hydrocarbon from the sorbent.

12. The apparatus of claim 11 wherein the means for desorbing comprises:
a heater located adjacent the sorbent for desorbing the at least one hydrocarbon from the sorbent by raising the temperature of the sorbent, and
a switch for activating and deactivating the heater.

13. A method for detecting a burial site of human remains, the method comprising:
providing an apparatus comprising a housing for containing sensor electronics, and an air intake conduit including a snorkel positioned upstream of the housing, and a sensor positioned in the snorkel upstream of the housing at an end section of the snorkel opposite the housing and positioned spaced downstream from an end of the snorkel;

drawing an air stream through the air intake conduit from locations near potential burial sites of human remains; and monitoring the air stream in the snorkel with the sensor to determine whether in the air stream there is present an indicator compound selected from the group consisting of halogenated compounds, hydrocarbons, nitrogen-containing compounds, sulfur-containing compounds, acid/ester compounds, oxygen-containing compounds, and naphthalene-containing compounds, wherein determining that the indicator compound is present in the air stream indicates a burial site of human remains.

14. The method of claim 13 wherein the the apparatus includes a hydrocarbon sensor and a halogen sensor, and the hydrocarbon sensor is located upstream of the halogen sensor.

15. The method of claim 13 further comprising:
recording a concentration level of indicator compounds at the locations near potential burial sites.

16. The method of claim 13 wherein:
the step of monitoring the air stream comprises providing a sensor in the snorkel of the air intake conduit, the sensor being in electrical communication with an indicator that signals when the sensor has detected the presence of the indicator compound in the air stream.

17. The method of claim 13 wherein the sensor is in electrical communication with a visual indicator that lights up when the sensor has detected the presence of the indicator compound in the air stream.

18. The method of claim 13 wherein the sensor is in electrical communication with an audible indicator that emits an audible signal when the sensor has detected the presence of the indicator compound in the air stream.

19. The method of claim 13 wherein:
the indicator compound is a halogenated compound, and
the sensor is a halogen sensor the halogen sensor being in electrical communication with an indicator that signals when the halogen sensor has detected the presence of the halogenated compound in the air stream.

20. The method of claim 13 wherein:
the indicator compound is a hydrocarbon, and
the sensor is a hydrocarbon sensor, the hydrocarbon sensor being in electrical communication with an indicator that signals when the hydrocarbon sensor has detected the presence of the hydrocarbon in the air stream.

21. The method of claim 13 wherein the step of monitoring the air stream comprises:
concentrating the indicator compound in the air stream before the air stream contacts the sensor.

22. The method of claim 21 wherein:
the indicator compound is concentrated in the air stream by adsorbing the indicator compound on a sorbent and thereafter desorbing the indicator compound from the sorbent.

23. A method for detecting a burial site of human remains, the method comprising:
providing an apparatus comprising a housing for containing sensor electronics, and an air intake conduit including a snorkel positioned upstream of the housing, and a halogen sensor positioned in the snorkel upstream of the housing at an end section of the snorkel opposite the housing and positioned spaced downstream from an end of the snorkel, and a hydrocarbon sensor positioned in the snorkel upstream of the housing at the end section of the snorkel opposite the housing and positioned spaced downstream from the end of the snorkel;
drawing an air stream through the air intake conduit from locations near potential burial sites of human remains; and
monitoring the air stream in the snorkel with the halogen sensor to determine whether a halogenated compound is present in the air stream;
monitoring the air stream in the snorkel with the hydrocarbon sensor to determine whether a hydrocarbon is present in the air stream;
wherein determining that a halogenated compound or a hydrocarbon is present in the air stream indicates a burial site of human remains.

24. The method of claim 23 wherein the hydrocarbon sensor is located upstream of the halogen sensor.

25. The method of claim 23 further comprising:
recording a concentration level of halogenated compounds or hydrocarbons at the locations near potential burial sites.

26. The method of claim 23 wherein:
the halogen sensor is in electrical communication with an indicator that signals when the halogen sensor has detected the presence of the halogenated compound in the air stream, and
the hydrocarbon sensor is in electrical communication with an indicator that signals when the hydrocarbon sensor has detected the presence of the hydrocarbon in the air stream.

27. The method of claim 26 further comprising:
concentrating the halogenated compound or the hydrocarbon in the air stream before the air stream contacts the halogen sensor and the hydrocarbon sensor.

28. The method of claim 27 wherein:
the halogenated compound or the hydrocarbon is concentrated in the air stream by adsorbing the halogenated compound or the hydrocarbon on a sorbent and thereafter desorbing the halogenated compound or the hydrocarbon from the sorbent.

* * * * *